United States Patent
Haus (10) Patent No.: US 12,324,714 B2
(45) Date of Patent: Jun. 10, 2025

(54) METHOD FOR PRODUCING A DENTAL RESTORATION

(71) Applicant: NOBEL BIOCARE SERVICES AG, Kloten (CH)

(72) Inventor: Adrian Haus, Mahwah, NJ (US)

(73) Assignee: Nobel Biocare Services AG, Kloten (CH)

(*) Notice: Subject to any disclaimer, the term of this patent is extended or adjusted under 35 U.S.C. 154(b) by 0 days.

(21) Appl. No.: 16/093,060

(22) PCT Filed: Apr. 11, 2017

(86) PCT No.: PCT/EP2017/058662
§ 371 (c)(1),
(2) Date: Oct. 11, 2018

(87) PCT Pub. No.: WO2017/178479
PCT Pub. Date: Oct. 19, 2017

(65) Prior Publication Data
US 2019/0125502 A1    May 2, 2019

(30) Foreign Application Priority Data
Apr. 12, 2016    (EP) .................... 16164846

(51) Int. Cl.
*A61C 13/00* (2006.01)
*A61B 6/03* (2006.01)
(Continued)

(52) U.S. Cl.
CPC .......... *A61C 13/0006* (2013.01); *A61B 6/032* (2013.01); *A61B 6/51* (2024.01);
(Continued)

(58) Field of Classification Search
CPC ..... A61C 13/0006; A61C 5/77; A61C 9/0053; A61C 13/082; A61C 13/0004;
(Continued)

(56) References Cited

U.S. PATENT DOCUMENTS

| | | | |
|---|---|---|---|
| 9,861,457 B2* | 1/2018 | Fisker | G16H 50/50 |
| 10,595,966 B2* | 3/2020 | Carrier, Jr. | A61C 9/0053 |

(Continued)

FOREIGN PATENT DOCUMENTS

| | | | | |
|---|---|---|---|---|
| DE | 199 22 870 A1 | 12/2000 | | |
| EP | 3442463 B1 * | 11/2022 | ............. | A61B 6/032 |

(Continued)

OTHER PUBLICATIONS

International Search Report for Application No. PCT/EP2017/058662 mailed Jun. 16, 2017 in 2 pages (the ISR for the PCT Application of this US national phase application).

(Continued)

*Primary Examiner* — Darrin D Dunn
*Assistant Examiner* — Olvin Lopez Alvarez
(74) *Attorney, Agent, or Firm* — Knobbe, Martens, Olson & Bear, LLP (57) ABSTRACT

The present invention provides a method for producing a dental restoration for preferably at least a part of at least one tooth. The method comprises the step of obtaining design data, wherein the design data includes acquired data and preliminary design data of the dental restoration. The method further comprises the step of modifying the preliminary design data before at least one manufacturing step to obtain modified design data and producing the dental restoration based on the modified design data.

21 Claims, 5 Drawing Sheets

(51) Int. Cl.
  *A61B 6/14*   (2006.01)
  *A61B 6/51*   (2024.01)
  *A61C 5/77*   (2017.01)
  *A61C 9/00*   (2006.01)
  *A61C 13/08*  (2006.01)
  *G05B 19/4099* (2006.01)

(52) U.S. Cl.
  CPC .............. *A61C 5/77* (2017.02); *A61C 9/0053* (2013.01); *A61C 13/0004* (2013.01); *A61C 13/0022* (2013.01); *A61C 13/082* (2013.01); *G05B 19/4099* (2013.01); *G05B 2219/35134* (2013.01); *G05B 2219/49007* (2013.01)

(58) Field of Classification Search
  CPC ....... A61C 13/0022; A61B 6/032; A61B 6/14; G05B 19/4099; G05B 2219/35134; G05B 2219/49007
  See application file for complete search history.

(56) References Cited

U.S. PATENT DOCUMENTS

| | | | |
|---|---|---|---|
| 11,510,759 B2* | 11/2022 | Fisker | A61C 13/0004 |
| 2004/0197727 A1* | 10/2004 | Sachdeva | A61C 13/0004 433/24 |
| 2005/0089822 A1* | 4/2005 | Geng | G06F 30/00 433/215 |
| 2005/0170315 A1 | 8/2005 | Strobel et al. | |
| 2008/0241798 A1* | 10/2008 | Holzner | A61C 13/0018 433/223 |
| 2009/0248184 A1* | 10/2009 | Steingart | G06F 3/016 700/98 |
| 2009/0319068 A1* | 12/2009 | Sager | A61C 8/0048 700/98 |
| 2010/0268363 A1* | 10/2010 | Karim | A61C 13/087 700/98 |
| 2011/0014586 A1* | 1/2011 | Jorneus | A61C 8/0075 433/173 |
| 2011/0171604 A1* | 7/2011 | Durbin | A61C 9/0053 433/213 |
| 2011/0196654 A1* | 8/2011 | Genest | A61C 13/0004 703/1 |
| 2012/0202008 A1* | 8/2012 | Garcia | B22F 3/12 428/143 |
| 2012/0291284 A1* | 11/2012 | Warden | A61C 13/0004 29/896.1 |
| 2013/0316302 A1* | 11/2013 | Fisker | A61C 13/0004 433/171 |
| 2014/0088929 A1* | 3/2014 | Suttin, Sr. | G06F 30/00 703/1 |
| 2014/0124374 A1* | 5/2014 | Eriksson | A61C 1/084 205/112 |
| 2014/0277665 A1* | 9/2014 | Fisker | G06F 30/00 700/98 |
| 2014/0308624 A1 | 10/2014 | Lee et al. | |
| 2015/0125822 A1* | 5/2015 | Cramer Von Clausbruch | A61C 13/082 433/202.1 |
| 2015/0238290 A1* | 8/2015 | Wouters | G05B 15/02 700/98 |
| 2015/0282905 A1* | 10/2015 | Jahns | C04B 35/63488 433/167 |
| 2016/0242881 A1* | 8/2016 | Fisker | A61C 13/0004 |
| 2016/0262860 A1* | 9/2016 | Korten | G16H 20/40 |

FOREIGN PATENT DOCUMENTS

| | | | |
|---|---|---|---|
| JP | H09-19443 A | 1/1997 | |
| JP | 2009-536056 A | 10/2009 | |
| JP | 2016-30158 A | 3/2016 | |
| JP | 6901496 B2 * | 7/2021 | ............. A61B 6/032 |
| WO | WO 2012/049879 A1 | 4/2012 | |

OTHER PUBLICATIONS

Japanese Office Action for Japanese Patent Application No. 2018-549221, dated Feb. 5, 2021 in 11 pages including English translation.

* cited by examiner

Fig. 1

PRIOR ART

METHOD FOR PRODUCING A DENTAL RESTORATION

CROSS-REFERENCE TO RELATED APPLICATIONS

This application is a national stage application under 35 U.S.C. § 371 of International Application No. PCT/EP2017/058662, filed on Apr. 11, 2017, which published in English as WO 2017/178479 A1 on Oct. 19, 2017, and which claims priority benefit of EP patent application Ser. No. 16/164,846.4, filed on Apr. 12, 2016.

TECHNICAL FIELD

The present invention relates to a method for producing a dental restoration.

BACKGROUND OF THE INVENTION

In recent years, there has been a trend towards treatments and dental restorations in dentistry that are customized to the individual patient. This customization resulted in products that particularly aim to provide optimized solutions in terms of appearance and function. These treatments mostly require additional and complex machinery and expertise or a high amount of manual work. As a result, there has been a constant challenge to reduce costs for these customized treatments, also to make them more widely available.

One important aspect in reducing costs is to reduce the man hours or manual work spent on these dental treatments. This is partly achieved by an increase in machining using above-mentioned additional machinery. Nonetheless, although this increased use of machinery is able to replace manual work, it primarily increases the quality of dental restorations, which has formerly been significantly dependent on the skills of the respective technician.

In terms of individualization and quality, the additional machinery is normally used alongside integrated computer aided design and manufacturing techniques, widely known as CAD/CAM. However, this integration is confronted with numerous different systems and workflows. As a consequence, improvements are often only applicable for very specific workflows and machinery.

The workflows in place in today's markets are numerous. For example, the traditional workflow between a dentist and a dental lab still exists although this workflow has been, for example, partly replaced by dentists performing machining in their own practice, the so-called chair side milling. Another workflow that is used nowadays centralizes production at an industrial site. This workflow primarily achieves cost reductions by volume and facilitates the use of specialized machinery that is too expensive for a dental lab let alone a dental office.

Nonetheless, these workflows have a general common pattern concerning the timing of their steps. More specifically, the production process of a dental restoration starts with obtaining data from a patient, followed by designing the dental restoration. Based on this design, the dental restoration is manufactured and the manufactured restoration is verified.

For example, U.S. Pat. No. 8,521,317 B2 uses a dental CAD/CAM system to provide a prosthetic dental item with desired aesthetic properties using structural analysis. In order to manufacture this functionally and aesthetically optimized dental item, the system places the item in a milling block according to the desired design determined in the previous step. Thus, once the design is finished, it depends on the manufacturing process to find a cost efficient way to manufacture the dental restoration. Although such a system may be able to provide a prosthetic dental item that will be hardly recognized as such in the mouth of a patient, cost savings can only be achieved within the individual steps of the workflow once it is integrated using CAD/CAM.

Similarly, US 2015/0086939 A1 discloses a method for producing a dental restoration, wherein a data flow starts with a 3D-scan of a restoration site of a patient's mouth. Based on this 3D-scan, a computer-aided design of the dental restoration is obtained and in turn, based on this design, the restoration is then milled. Based on the position of the restoration during milling, the milled restoration is transferred to retention means so that this step provides position information of the restoration relative to a post-processing machinery for removal of sprues or coloring based on the CAD-Design. Again, cost improvements are limited to the individual steps of the production process.

SUMMARY OF THE INVENTION

Consequently, the objective of the present invention is to provide a method for producing a dental restoration that is more cost effective without having a significant effect on the quality of treatment. Another objective is to make these individualized advanced dental treatments more widely available to patients. Finally, the method should be capable of being applicable to a variety of workflows.

These objectives resulted in the following method for producing a dental restoration according to the independent claim, wherein preferred embodiments are defined in the dependent claims.

The present invention provides a method for producing a dental restoration of preferably at least a part of at least one tooth comprising the steps of obtaining design data of the dental restoration, wherein the design data comprises acquired data and preliminary design data; modifying the preliminary design data, in particular at least partly based on the acquired data, before execution of at least one manufacturing step to obtain modified design data, and manufacturing the dental restoration based on the modified design data.

The idea to include acquired data in the production process of a dental restoration, i.e. initial data about the dental situation of a patient, originates from the realization of the inventors that one of the shortcomings of existing production processes for a dental restoration is fixing or locking the design of the dental restoration already in the design phase prior the manufacturing phase. As a result, the subsequent manufacturing steps after fixing the design as well as the placement of the dental restoration cannot make use of their full potential in terms of reducing the costs associated with providing the dental restoration.

In contrast, the acquired data, which this method includes in the design data, provides the option to steps of the workflow subsequent to the design step to influence the design and alter the outcome of the dental restoration in terms of quality and in particular in terms of costs. More specifically, with the present invention it is possible to modify and/or optimize the data of a preliminary design of a dental restoration due to the availability of the acquired data and in view of at least one upcoming manufacturing step.

In other words, the final design of the dental restoration is not only created during the design phase but accompanies the production process preferably at least until the at least one manufacturing step. At this at least one manufacturing step, the preliminary design data can still be modified in order to achieve the desired optimization of the dental restoration. Thus, the modification step can be done prior each manufacturing step or as a pre-manufacturing modification for at least two and preferably all manufacturing steps.

As a result of this method, manufacturing costs can be reduced by shortening production cycles through leveraging the full potential of the manufacturing equipment used. In a nutshell, the optimization of production is done not only during the design phase but also at the site of manufacturing, where knowledge about how to effectively produce a dental restoration is more readily available.

Further, the method according to the invention can be applied to any workflow since it concentrates on improving one of the fundamental aspects of providing a dental restoration, namely the data itself, particularly by including acquired data and preliminary design data, as well as the data flow throughout the production process.

In a preferred embodiment, the acquired data includes placement information, in particular comprising the position and/or orientation of the at least one tooth of the dental restoration.

This embodiment provides placement information of the at least one tooth as part of the acquired data. The placement information may include the position and/or orientation of the at least one tooth, wherein the position of the tooth is preferably the tooth number as commonly used in dentistry. However, the position of a tooth may also be expressed as coordinates in relation to the upper and/or lower jaw bone of the patient. Further, the orientation of the at least one tooth to be restored may also be included. Both the position of a tooth or dental restoration as well as its orientation provide information about the visibility of different sections of the dental restoration to be manufactured.

The placement information is of particular value during manufacturing since it can be used to determine the precision needed for different parts of a dental restoration. As a result, the costs for manufacturing the dental restoration can be reduced by increasing the speed of production and employing high precision tools and/or techniques only where necessary.

In another preferred embodiment, the placement of support means, in particular a support pin, for supporting the dental restoration during handling and/or production is automatically determined based on the placement information.

In the meaning of the present invention, a support pin is used to connect the dental restoration to the blank during production, i.e. during milling and/or sintering.

This embodiment has particularly the advantage that it allows for a cost reduction during manufacturing as well as improved aesthetics. More specifically, the support means are advantageously placed during manufacturing in order to achieve sufficient mechanical characteristics for the support and the restoration and/or optimized aesthetics for the restoration.

In particular, the support means are placed on the lingual side of the dental restoration. Alternatively, the support means can be placed on other non-visible surfaces of the dental restoration at intended use; said other non-visible surfaces can e.g. be at least one of a non-visible interdental side facing an adjacent tooth, a buccal side of a molar and/or pre-molar and the surface of the last molar at the end of the dental arch facing away from the adjacent tooth.

For example, the aesthetics may be optimized so that after removal of the support means during manufacturing, the former connection points of the supporting means to the dental restoration do not have an adverse effect on the aesthetics of the restoration. Another parameter that may be used for optimizing the manufacturing step is the placement of the support means at a position that facilitates easy removal of the support means.

Any support means of the dental restoration to be manufactured is preferably added to the preliminary design of the dental restoration at the beginning of the manufacturing step. This way all aspects of manufacturing may be taken into account down to quality control to provide an optimized placement of the support means.

In another preferred embodiment, the placement information comprises at least one of the following information: buccal side; lingual side; visible portion; interdental space, area of contact to other teeth.

This embodiment basically provides information or data that is particularly useful for an optimization of the dental restoration in order to reduce the total costs for providing this treatment to a patient, again independent of the general workflow.

For example, any one of these parameters, which identify the orientation of different sections of a restoration, allows for setting parameters such as surface roughness, level of detail, coloring and/or grading of different portions belonging to a dental restoration. The objection is to achieve the desired aesthetic appearance and at the same time to avoid an unnecessary finish of the remaining portions of the dental restoration.

For example, faces that will not be visible if the dental restoration is placed in the patient's mouth may well have a rougher surface and/or a lower level of detail than a visible surface. Also, the chewing surface does not have to be as smooth as a visible buccal surface of the dental restoration. In other words, this embodiment allows for visible parts of a dental restoration to be manufactured in terms of functionality and aesthetics, whereas non-visible parts of a dental restoration are primarily focused on functionality.

In particular, the method comprises the step of manufacturing, in particular milling, the occlusal surface of at least one of the molar teeth and the pre-molar teeth to a higher level of detail than for the other teeth, in particular the canine teeth and/or incisor teeth.

Preferably, the placement information comprises information about the level of detail of the occlusal surface, in particular dependent on the position of the tooth.

This embodiment allows for providing the necessary structure to the occlusal surface of the teeth depending on their function and/or position while allowing for a cost efficient manufacturing process.

As is know in the art, the surface structure of the occlusal surface of the molar and/or pre-molar teeth is relevant e.g. during the chewing process, wherein the surface structure of the other teeth, in particular canine teeth and/or incisors, is not as relevant for said function and also not very relevant for aesthetic purposes.

In the meaning of the present invention, a restoration having higher level of detail means that small irregularities in the restoration surface like depressions and/or grooves originating from the natural tooth are reproduced more faithfully than for other restoration having lower level of detail.

In another preferred embodiment, the method comprises the step of manufacturing, in particular milling, the buccal side of the at least one tooth with higher precision and/or a higher level of detail than the lingual side.

This embodiment is a particular easy implementation of the invention's method, which, nonetheless, proved to be very cost effective. This is even more the case if this embodiment is applied only to frontal teeth. Higher precision is generally achieved by decreased manufacturing tolerances and/or the use of smaller tools to achieve reduced surface roughness and/or higher level of detail. The level of detail is basically the accuracy in copying or imitating the outer shape of natural tooth. For example, the surface of the dental restoration on the lingual or an interdental side can be designed smoother in terms of its general geometry so that small irregularities in the restorations surface like depressions or grooves as present on a natural tooth are removed.

A more efficient design according to this embodiment can also be achieved by manufacturing a part of the surface of an interdental space at its border to the buccal side with higher precision and/or a higher level of detail.

In contrast, the lingual side may be manufactured with less precision and/or lower level of detail compared to the buccal side. Alternatively or in addition, the occlusal surface of at least one tooth, in particular at least one of the canine teeth and/or incisor teeth, may be manufactured with less precision and/or less detail than the occlusal surface of at least one of the molar teeth and the pre-molar teeth. This can also or alternatively apply to the part of the surface of the interdental space, which directly faces, i. e. in a direction normal to that surface, the interdental face of the adjacent tooth so that this part is hardly visible when looking at the patient during everyday life.

In another embodiment of the method, it comprises the step of verifying the dental restoration, wherein the placement information is used to place the dental restoration in a measurement device in a required position to obtain measurement data by measuring the dental restoration.

By including the verification of the dental restoration, the aforementioned support means can be placed to avoid any repositioning or blind spots during verification. Preferably the support means is placed so that repositioning is neither necessary for manufacturing nor for verifying the manufactured dental restoration. Consequently, this embodiment provides a particular fast and reliable verification or quality control. This is particular the case, if verification takes place at the same facility and preferably even without any chucking or clamping between manufacturing and quality control.

In another particularly preferred embodiment of the method, the verifying step comprises comparing the measurement data and the design data and/or data derived from the design data, in particular from the acquired data, to obtain at least one acceptability criterion.

This acceptability criterion provides comprehensible fast basis for a decision, in particular an automatic decision, if the quality of a dental restoration suffices for placement in a patient. If a dental restoration fails the acceptability criterion, it may further be used to decide if the dental restoration can still be post-processed to render it acceptable for placement.

A preferred acceptability criterion is directed to the precision of manufacturing at an interface region of the dental restoration used for placement of the restoration in the mouth of the patient. This ensures a proper seating and fixation of the dental restoration.

The criterion may at least partly be derived from acquired data, the preliminary design data of the dental restoration and/or modified design data that has been as explained above. Using acquired data has the advantage to directly compare the dental restoration to the actual dental situation of a patient. Further, since the criterion may also be derived from manufacturing data, it can be designed to concentrate on characteristics that are specific to a manufacturing technology that is used for a dental restoration. In particular, the acceptability criterion can be directed to specific characteristics of this manufacturing technology. Further the criterion may indicate the need for adjustment of manufacturing equipment or may be used for long-term improvements of the production process or workflow.

In a further particularly preferred embodiment, the design data, preferably the acquired data, comprises shading data and/or color data of the at least one tooth.

This data may serve to perform an optimization of aesthetic appearance of a dental restoration in relation to the manufacturing techniques that are applied. For example, this data may be used in order to select or manufacture a blank, i. e. the shading data and/or color data may be used in this embodiment to determine the desired characteristics of a pre-shaded blank.

The shading and/or coloring data may also serve as basis during manufacturing of the dental restoration to account for an additional thickness of a specific manufacturing technique that may be applied during shading and/or coloring of a dental restoration.

Further, the shading and/or coloring data comprised in the acquired data may include information from the at least one natural tooth that is to be replaced or of at least one neighboring or opposite tooth.

In another preferred embodiment of the method, the method comprises a step of providing data representing a blank comprising at least a portion made of a multilayered material and selecting a part of the blank based on the shading data and/or color data to produce the dental restoration from the blank.

Using this technique also reduces costs. There are less blanks necessary since different dental restorations can be positioned in a blank to achieve their respective desired aesthetical and/or functional characteristics. In other words, one dental restoration with a desired shading and/or coloring can be manufactured from a first section of a pre-shaded and/or pre-colored blank, wherein another dental restoration with a different desired shading and/or coloring can be manufactured from another section of the same pre-shaded and/or pre-colored blank. Pre-shaded and/or pre-colored blanks are advantageous since they can be produced in high numbers and are not custom-made for only one patient. Thus, one pre-shaded and/or pre-colored blank can serve as a workpiece for different dental restorations.

It is possible to implement this embodiment at different parts of the workflow. For example, the color may already be chosen as part of the preliminary design and/or comprised in the acquired data, whereas the shading is decided during modification of the preliminary design at manufacturing. However, it is also possible to perform both steps during manufacturing or during creation of the preliminary design. In the latter case, it is preferred that information about pre-shaded and/or pre-colored blanks is available to the designer.

Even more preferably the dental restoration is produced from a part or portion of a blank that is determined on the basis of the shading and/or color of a visible portion of the dental restoration as comprised in the design data.

Preferably, the method comprises a step of providing data representing a blank comprising at least a portion made of a multilayered material and selecting a part of the blank based on a visible representation of the dental situation comprised in the design data. The visible representation can be part of the acquired data and/or the preliminary design data.

This embodiment is particularly advantageous in combination with above noted placement information since a patient-specific dental restoration to be manufactured can be positioned in a pre-shaded and/or pre-colored blank in order to achieve an optimized result in relation to visible parts of the dental restoration. As described above, visible parts refer to externally visible parts and is in particular the buccal side of the dental restoration and even more preferably the buccal side of the frontal teeth. In other words, the same pre-shaded and/or pre-colored blank may be used for even more different dental restorations since aesthetics of each dental restoration is finally primarily dependent on the fact if it is visible or not.

In another preferred embodiment of the method, it comprises the step of providing the design data, wherein the design data including the acquired data are preferably generated with a computer program.

This embodiment is particularly advantageous for an integrated CAD/CAM workflow. It reduces the manual entry of data to a minimum. For example, placement information such as the tooth number may be provided through techniques like shape recognition instead of a dentist or a technician manually entering this data. Applying this embodiment also prevents mistakes that occur due to manual data entry.

In another particularly preferred embodiment of the method, the acquired data of the design data are based on at least one of scan data, a photo and manually entered data of a dental situation of a patient.

Preferably, the scan data comprise intra-oral scan data or extra-oral scan data. In particular, the extra-oral scan data are generated with at least one of CT scanning and scanning of a model or impression of the dental situation of the patient.

Acquired data basically include information that is obtained from a patient by means of scanning at least the location, where the dental restoration is to be placed, and/or data acquired by a dentist and/or other dental professional, which are entered manually into the system such as a tooth number. A scan may be performed intra-orally in the mouth of a patient or an extra-oral scan using for example CT-scanning or an impression of a patient's dental situation. A CT-scan has the advantage to also provide reliable data concerning the bite of a patient.

Preferably, the scan includes the at least one natural tooth that is to be replaced by the dental restoration. The scanning technique may also provide data concerning shading and/or coloring of the at least one tooth to be replaced and/or at least one adjacent tooth. If the latter is included in a scan, it is further possible to provide a dental restoration that has a more reliable fit and is aesthetically better adapted to the dental situation of a patient. Both reduce the chair time needed for a patient.

As described above, the data provided by a scan is also particularly useful for deriving an acceptability criterion for performing a quality check. Further, the scanned data may also be used to verify the final result of treatment after the dental restoration is placed in the oral cavity of a patient.

According to this preferred embodiment, the scan data can be a combination of a photo, intra-oral scanning, CT scanning and/or scanning a model or impression of the dental situation of the patient.

This has the advantage that a combination of two or more data acquisition techniques can be combined to obtain more detailed and complete information of a patient's dental situation concerning shading, color, position, orientation and/or occlusion for a dental restoration.

In another preferred embodiment of the method, the dental restoration is placed after production without veneering to obtain a desired shading and/or color of the at least one tooth. Naturally, at least one of a staining, glazing and polishing step can be performed optionally on the dental restoration before placing the dental restoration.

This embodiment basically eliminates manual work that might be needed in manufacturing the dental restoration. It is in particular advantageous if applied together with above described placement of the dental restoration to be manufactured within a pre-shaded blank.

In summary any embodiment of the present invention is able to reduce costs through a more efficient use and reuse of design data and in particular by allowing further modifications of the design of a dental restoration after a preliminary design is obtained.

BRIEF DESCRIPTION OF THE FIGURES

The following figures illustrate the prior art and preferred embodiments of the present invention. The latter are not to be construed as limiting but merely to simplify the understanding of the invention together with the following description. In these figures, identical reference signs refer to parts of the embodiments having the same or an equivalent function and/or structure, wherein.

DETAILED DESCRIPTION OF PREFERRED EMBODIMENTS

Figure 1:
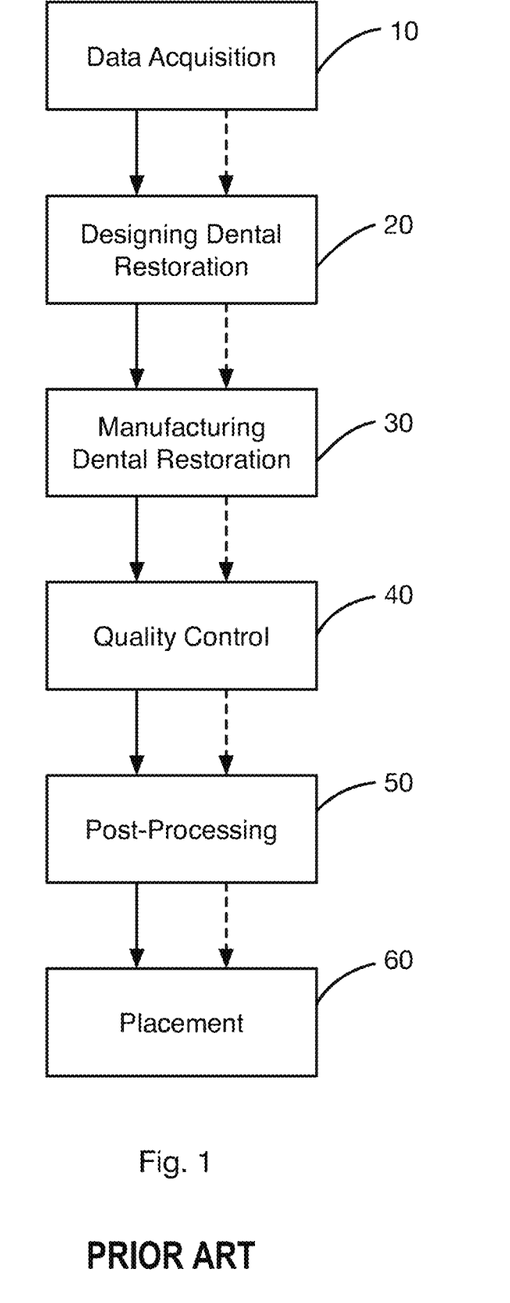
FIG. 1 shows a flow chart illustrating the general workflow of a production process for providing a dental restoration according to the prior art.

FIG. 1 shows a workflow for providing or producing a customized dental restoration. As explained above, this workflow is common to various methods for providing a dental restoration.

First, patient specific data is collected in a data acquisition step 10, which forms the basis for the dental restoration. The patient specific data is then used to create a design of the dental restoration in a dental restoration design step 20. All the information that defines the dental restoration is included in the design phase such as geometry, coloring, shading, dimensions, tolerances for manufacturing, etc. This information is afterwards used during a manufacturing phase comprising a manufacturing step 30 to manufacture the dental restoration, followed by a quality control step 40, which determines if the aesthetic and functional characteristics of the product are as desired. At the end of the manufacturing phase, a post-processing step 50 finishes the dental restoration so it can be placed in the mouth of a patient in placement step 60.

Since the data acquisition 10 and the placement of the restoration 60 require the presence of the patient, these steps are generally done at a dentist's office. In contrast, the step of designing a dental restoration 20, manufacturing that dental restoration 30, performing quality control 40, and post-processing the resulting dental restoration in step 50 may be done at the dentist's office, a dental lab or an industrialized manufacturing site. One of the advantages of the present invention's method is that it can provide a significant improvement to the process of providing a dental restoration independent of where these general steps are performed.

This is primarily achieved by the way data is provided and exchanged. In the workflow of the prior art shown in FIG. 1, information flows from step to step as indicated by the arrows with dashed lines. Since the design of the dental restoration is fully established in design step 20, there is no need to add additional data to the flow of information. Quite the opposite is the case, namely that information is not carried on to subsequent steps but removed from the information flow. More specifically, loss of information occurs when only processed information is transferred between steps of a workflow as illustrated in FIG. 1. This particularly happens if the execution of two successive steps takes place at different locations. For example, the data acquisition step 10 is performed at the dentist's office, whereas the design of the dental restoration 20 is provided by a dental lab. However, removal of data and in particular the removal of acquired patient data renders it impossible to use this data for reducing costs in the process of providing a dental restoration.

Figure 2:
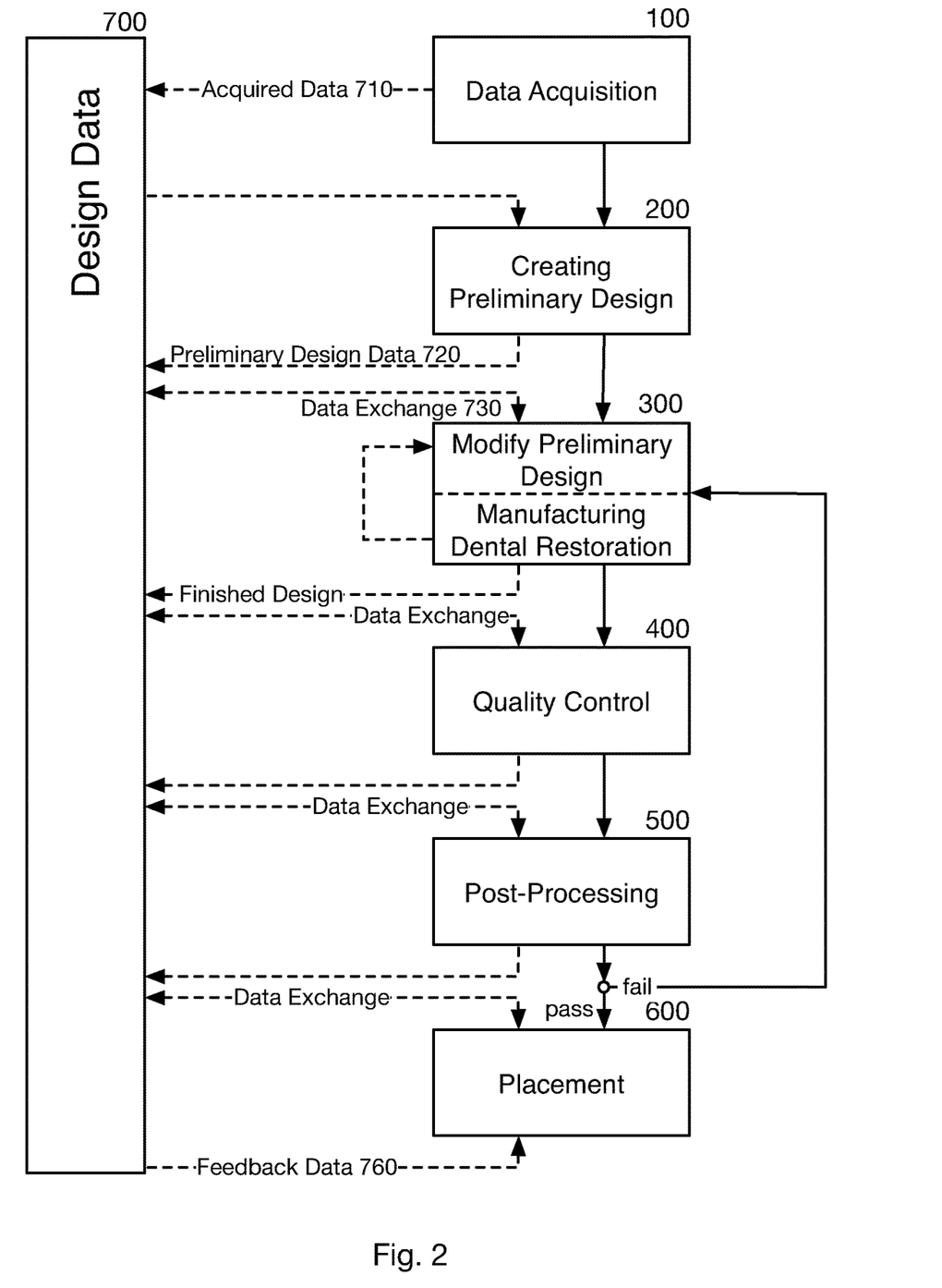
FIG. 2 shows a flow chart illustrating a workflow for a production process of a dental restoration according to the present invention used for providing a dental restoration.

This observation gave the inventors of the present method, illustrated in the flow chart of FIG. 2, the idea to provide in particular the acquired patient data as part of the design data 700 obtained in a data acquisition step 100 to achieve an effective production of a dental restoration. In a nutshell, the method keeps information or data that can be used in subsequent steps to drive down costs as explained in the following in relation to several examples.

Preferably, the design data 700 can be accessed in any step of the workflow to optimize the production process. Access to this information may be used to adapt or change manufacturing techniques in order to render the production process more cost efficient without an adverse affect on the quality of the treatment.

The data acquisition step 100 in FIG. 2 is in general similar to the data acquisition step 10 shown in FIG. 1 in relation to the prior art. However, in contrast to the data acquisition step 10 of the prior art, the information collected during data acquisition in step 100 is included in the design data 700.

In the data acquisition step, data for obtaining a dental restoration is collected. This data includes at least information about the section of the teeth of a patient that is to be replaced by the dental restoration. This section may be a part of one tooth such as a crown or comprise a complete tooth or several teeth. Further information may be included in the design data 700 by manual data entry and/or can be derived from a scan of the patient's oral cavity.

A scan provides an easy way to obtain the geometrical data or shape for building a restoration. Depending on the dental situation of a patient, the scan may provide the shape and appearance, i.e. color and/or shading, of the at least one tooth that is to be replaced. If the section that needs replacement is already missing, a scan of the same section on the opposite side may also be used to obtain shape and appearance. The appearance may also be derived from adjacent teeth. Thus, the data acquisition step 100 preferably obtains data from the whole oral cavity of a patient but at least from the restoration section and at least one adjacent tooth.

Further, using intra-oral scanning techniques or a CT-scan as extra-oral scanning technique is considerably more convenient for a patient than other techniques such as performing an impression. Nonetheless, it is also possible to obtain an impression or model for providing the scan data for a restoration. Further, scanning techniques may be combined to enhance the information base of the dental situation of a patient.

As mentioned above, the data collected by scanning may be used as a basis to derive other parameters. Thus, these parameters do not have to be entered manually or may be double checked using the derived value. For example, placement information such as position and/or orientation of the at least one tooth to be replaced can be identified by shape recognition. Double checking with a value manually entered has the advantage that a mismatch between the automatically derived value and the manually entered value may indicate an exceptional dental situation, which may need special attention.

The design data is accessed in the next step of the method 200, where a preliminary design of the dental restoration is created. As the term preliminary design indicates, the design is not a fixed design like the one obtained in the dental restoration design step 20 of FIG. 1. For example, information that is later on used in the manufacturing step 300 is not yet determined or at least not yet fully determined. Instead, the design may be modified in subsequent steps of the workflow, particularly to reduce costs.

Using a preliminary design is particularly advantageous in situations, where decisions on the design are dependent on the manufacturing techniques used to manufacture the dental restoration. For example, manufacturing may take place in relation to a machined blank that still has to be sintered or post-processed for obtaining its final dimensions. Thus, it is of advantage to perform fine adjustments at the manufacturing site, where information about a respective manufacturing method is more readily available.

Although the design can be manipulated throughout the production process, i. e. during manufacturing 300, quality control 400 and/or post-processing 500, there is no increased risk of producing a poor or defective dental restoration compared to the technique of fixing the design at an early stage since the design data 700 is always accessible so that inadequate parameters that may result in a dental restoration that does not fit can be prevented.

As indicated in FIG. 2 by the arrow with a dashed line, the data of the preliminary design 720 is added to the design data 700. At this stage of the workflow, the design data 700 consequently includes acquired data 710 as explained above as well as a preliminary design data 720 of the dental restoration.

Figure 3:
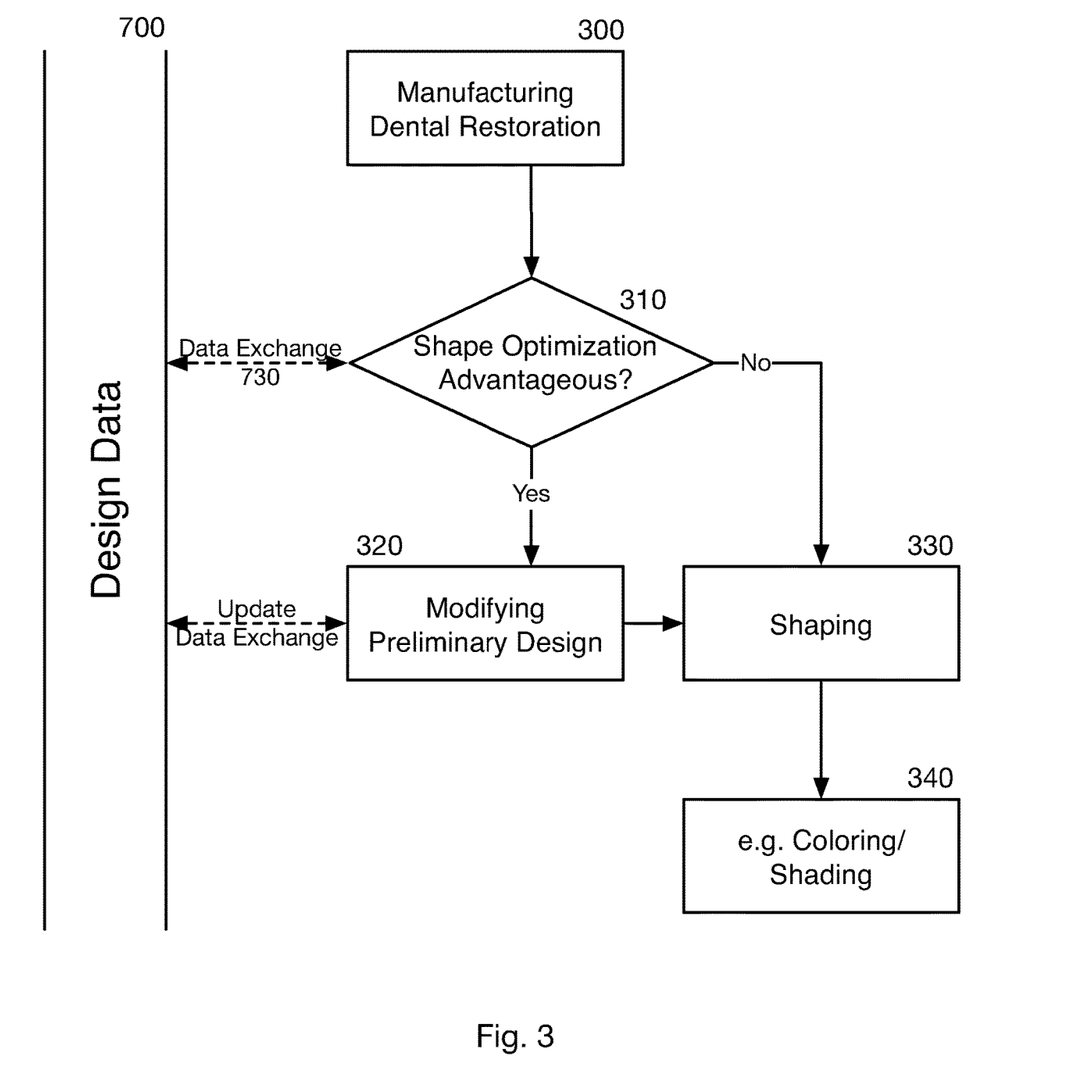
FIG. 3 illustrates a section of the workflow of FIG. 2 for more details about manufacturing the shape of a dental restoration in more detail.
Figure 4:
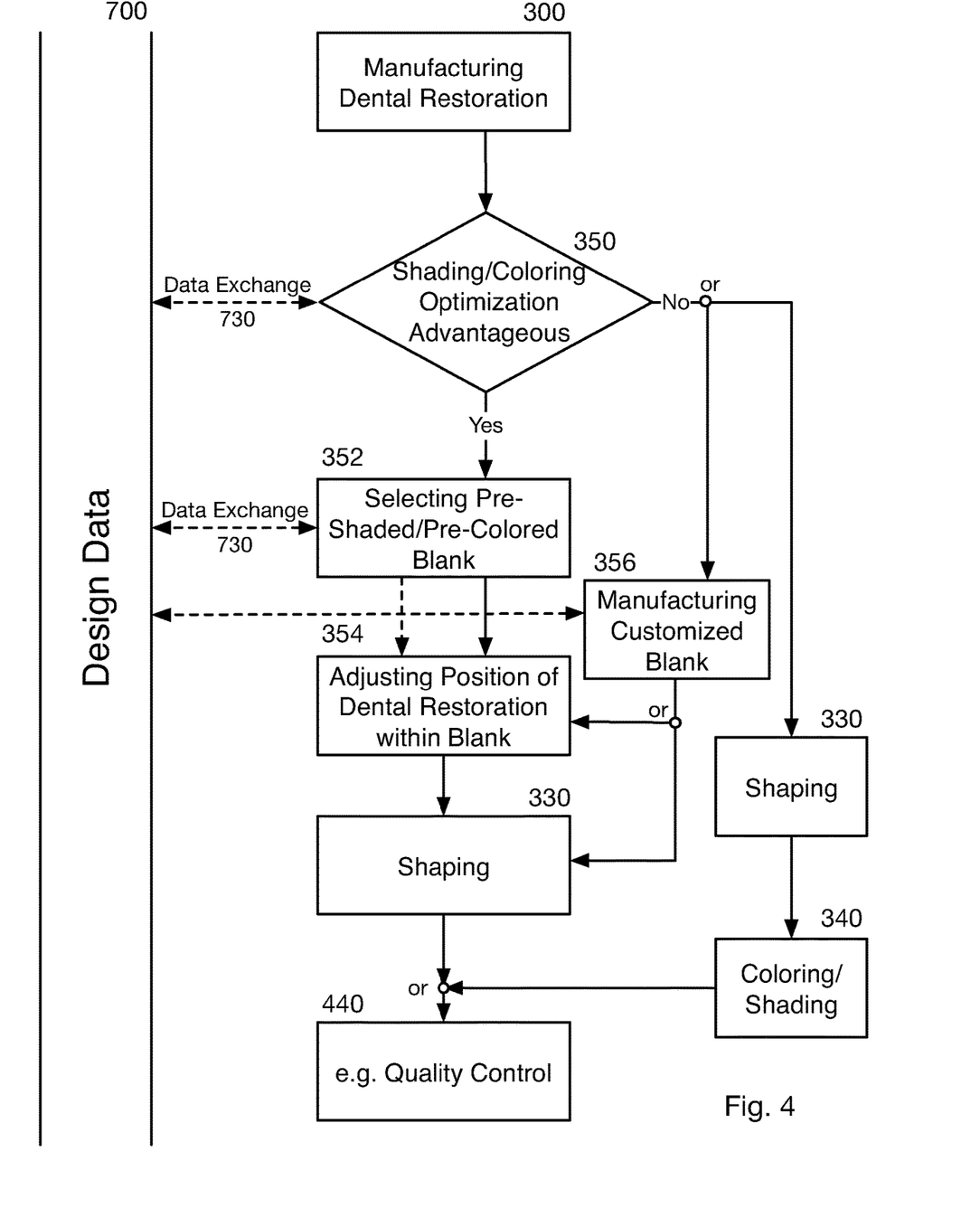
FIG. 4 is a detailed flowchart for illustrating shading and/or coloring of a dental restoration using design data to optimize the workflow of the production process.

Moving on to manufacturing step 300, at first, a data exchange between the manufacturing step 300 and the design data 700 is performed. Based on this data, it is decided if the preliminary design is to be modified in manufacturing step 300. As explained, this decision can be done before each manufacturing step or technique but is preferably done for all manufacturing steps before the actual manufacturing begins. Exemplary procedures for shaping and coloring/shading are shown in FIGS. 3 and 4, respectively.

In the beginning of manufacturing step 300, the preliminary design may be modified in step 310 in order to supplement or change the design data 700. For example, shading of the dental restoration can be supplemented to the preliminary design data 720 based on the acquired data 710 or changed in view of pre-shaded blanks that are available for manufacturing the dental restoration. More specifically, slight changes to the shading that are generally not recognizable once the dental restoration is placed in the mouth of a patient may allow the use of a pre-shaded blank instead of a customized one.

Other modifications in order to optimize manufacturing may comprise smoothing of at least one edge and/or surface, optimization of an interdental space, optimization of an occlusal detail, pin placement and/or positioning in a blank.

Any modification of the preliminary design data 720 may be performed prior a particular manufacturing step. However, it is preferred to perform all modifications prior actual manufacturing. Particularly at a manufacturing site, the manufacturing techniques that will be used can be determined at the beginning of manufacturing.

At the end of the manufacturing step 300, the dental restoration has been manufactured. Consequently, the design of the dental restoration is generally finished. However, there may be further changes to the design of the dental restoration depending on the outcome of step 400 that controls the quality of the manufactured dental restoration.

In the beginning of the quality control step 400, the design data 700 is consulted, for example, in order to determine an appropriate quality check procedure or to obtain the data for a quality check procedure. This way, the quality check can specifically react to characteristics of manufacturing techniques used to manufacture the dental restoration.

Preferably and as described above, the quality control obtains an acceptability criterion. Based on this criterion, the quality check step 400 can determine if the manufactured dental product passes or fails the required quality that may have been determined at the beginning of the step as a result of the initial data exchange.

If the manufactured dental restoration fails the quality check 400, the dental restoration may be returned to the manufacturing step 300, preferably with implemented changes of the design, in order to render the dental restoration acceptable.

If a dental restoration passes the quality check 400, the workflow may move on to a post-processing step 500. Alternatively, post-processing may already have been executed at least partly during the manufacturing step 300. Thus, there may be no separate post-processing step 500 necessary.

Independent of the point of time in the workflow, during post-processing 500, final adjustments are made to the dental restoration such as the removal of sprues and/or support means. Sprues and/or support means preferably result from a modification of the preliminary design obtained in the preliminary design step 200 at the beginning of the manufacturing step 300. Even more preferably, the support means are added to the preliminary design of the dental restoration taking the quality check that will be performed in step 400 into account. In this manner, the support means can be designed so that manufacturing and quality control can be performed as smooth as possible.

For example, if located correctly, the support means can keep the number of times the dental restoration has to be repositioned as low as possible. Similarly, the support means can prevent blind spots during quality control that would require re-clamping. If sprues are present, these are preferably also used as support means. Once post-processing 500 is done, the dental restoration can be placed in the placement step 600.

The dentist performing the placement 600 of the dental restoration preferably has access to the design data 700. In this manner, a dentist may perform a final check of the dental restoration in relation to the success of treatment and, if necessary, provide feedback data 760 to the design data 700. This has particularly the advantage that an assessment of the treatment's result is provided on the basis of objective design data 700.

After the end of treatment, the design data 700 may be used to optimize the production process so that systematic problems of a workflow can be identified that otherwise would be perceived as accidental. Consequently, the method of the present invention may also provide the means to continuously improve the production of dental restorations in the long run.

FIG. 3 shows the interaction of a shaping step 330, which is part of the manufacturing step 300, with the design data 700 in more detail. In the shaping step 330, the shape or geometry of the dental restoration is created using one of the manufacturing techniques known to the skilled person such as milling, molding or 3D-printing.

Although the shaping step 300 is shown as the first sub-step of the manufacturing step 300, it may also be a sub-step somewhere in the middle or at the end of the manufacturing step 300. The same applies to the coloring and/or shading step 340. Both general steps are merely shown in FIG. 3 to indicate the beginning and end of the shaping step 300 more clearly.

Further, after taking a decision if shape optimization is advantageous in step 310, the decision about shading/coloring optimization 350 or any other decision about a modification of the preliminary design may follow before actual manufacturing takes place. As explained above, this is particularly advantageous if several and preferably all manufacturing techniques can be determined before manufacturing begins.

In preparation for the shaping step 330, first a decision is made based on a data exchange 730 with the design data 700. More specifically, it is decided on basis of this data exchange 730 if any shape optimization is of advantage, also in view of the envisaged shaping method used in the shaping step 330. If the answer of this decision is "no", the workflow may directly move on to the shaping step 330 to manufacture the shape of the dental restoration based on the design of the dental restoration, which has been received by the previous data exchange of 730 or alternatively by accessing the design data 700 again.

If the decision is "yes" that shape optimization is advantageous, the workflow moves on to step 320 for adapting or modifying the preliminary design. For example, in the modification step 320, the precision for manufacturing different portions of a dental restoration can be determined. Preferably, this decision on precision is done using placement information of the dental restoration such as location and/or orientation. The location may be expressed by a tooth number that is commonly known as a means for identification in the art. Further placement information may be provided in the form of placement information of individual portions of a dental restoration. For example, the additional placement information can include the orientation of a portion of the dental replacement. The orientation of a portion of the dental replacement can be expressed as being on the buccal side, lingual side, chewing, i.e. occlusal, side or interdental side. The more specific the information, the better the precision for manufacturing a dental restoration can be determined.

For example, if a portion of a dental restoration is situated on the lingual side, less precision is needed since the lingual side is generally less visible to an observer looking at a patient. In contrast, the buccal side of a tooth, in particular of a frontal tooth, is generally more visible so that it is particularly important to take aesthetic considerations into account. Thus, manufacturing with a higher precision and/or level of detail of these portions of a dental restoration is preferred.

Cost savings can particularly be achieved in portions that are less or not visible when looking at a patient during everyday life since the manufacturing can be done faster and with less precision. This reduction in precision and/or level of detail can be a higher surface roughness and/or comprise a redesign of a single side or interdental side of the dental restoration.

For example, the surface of the dental restoration on the lingual or an interdental side can be designed smoother in terms of its general geometry so that small irregularities in the restorations surface like depressions or grooves originating from the natural state are removed. In this manner, the tool-path can be simplified and may be followed using a bigger tool.

Further, the surface roughness can be increased if a surface finish layer will be provided on top of the shaped dental restoration so that a rougher surface may provide a better basis for attachment of this layer.

Based on the modification of the preliminary design in step 320, the workflow can move on to shaping step 330 in order to generate the shape of the dental restoration according to the modified preliminary design. Further the modified preliminary design created in step 320 is provided as update to the design data 700.

FIG. 4 shows as part of the manufacturing step 300, how shading and/or coloring may be optimized. For the position of the shading and/or coloring process the same applies as for the shape optimization, i.e. the process described as follows may also be executed in the middle or at the end of manufacturing step 300.

In step 350, it is decided if an optimization of the shading and/or coloring of a dental restoration is advantageous. As basis for this decision, step 350 consults design data 700 by means of a data exchange or data transfer 730.

If step 350 results in the conclusion that a shading and/or coloring optimization is advantageous, the workflow moves on to step 352 for selecting a pre-shaded and/or pre-colored blank based on data obtained by the former data exchange 730 and/or direct access to the design data 700. The decision in terms of optimization and selection of a blank may be based on placement information as described above. Preferably, color and/or shading data obtained during the acquisition step 100 is accessed for the decision step 350 and/or the selection step 352. Once a pre-shaded and/or pre-colored blank of a multilayered material is selected in step 352, this information may be provided to the design data 700 as an update.

Having selected the blank in step 352, step 354 for adjusting the position of the designed or virtual restoration within the blank follows. In this step, the design of the dental restoration is placed within the selected pre-shaded and/or pre-colored blank in order to achieve the desired aesthetics.

The adjustment performed in step 352 is preferably based on placement information that is also retrieved from the design data 700, and in particular on placement information that indicates the visibility of a portion of the dental restoration to be manufactured. In this manner, the positioning of the dental restoration's design can take visibility into account, which allows for a further reduction of costs as previously described.

Once the position of the dental restoration is established in step 354, the workflow can move on to shaping step 330, where further optimization and design modifications may be performed as described in relation to FIG. 3.

If step 350 results in the conclusion that there is no advantage in an optimization of the shading and/or coloring of a restoration, the workflow moves on to step 356 or to step 330. One reason of a "no"-decision in step 350 is the realization that using a pre-shaded and/or pre-colored blank will result in unsatisfactory aesthetics of the dental restoration. Thus, steps 356 and 330 are used as alternative workflows to manufacture a dental restoration with aesthetics as desired.

In step 356, a customized blank is manufactured on the basis of data that is obtained from design data 700. Once the customized blank is manufactured, the position of the virtual design within the customized blank may be adjusted as in step 354 before moving on to shaping step 330 and quality control step 400.

Alternatively, the workflow may directly continue to the shaping step 330 after the "no"-decision in step 350 in order to obtain a dental restoration that may then be processed for coloring and/or shading in step 344 using a technique that obtains the desired aesthetics. Examples for such techniques are staining and glazing.

Visibility of portions of a tooth or dental restoration refers to the influence of these portions on the aesthetics of the dental restoration. More specifically, visibility refers to the visibility of portions of a restoration when looking at a patient in everyday life. In this manner, imperfections of the dental restoration, e. g. resulting from cost saving measures, stay hidden and do not adversely affect neither the functionality nor the aesthetics of a dental restoration.

The visibility of different portions of the restoration may be classified as described above in relation to placement information. In this respect a tooth identifier can be used to indicate the precision of manufacturing needed. For example, a molar is generally less visible than a frontal tooth.

This information about visibility may be supplemented by specifying the orientation of a dental restoration's portion. For example, the lingual side of a tooth is less visible than the buccal side, in particular in terms of the frontal teeth. Concerning molars, however, the buccal side may be less visible than the corresponding lingual side. Portions of a dental restoration that are situated in an interdental space are in general hardly visible.

In general, visible portions of a dental restoration are produced taking into account functionality and aesthetics, whereas non-visible or hardly visible portions are primarily produced in terms of functionality. For example, the interface for attaching a dental restoration is not visible and is, thus, only manufactured in terms of functionality, in particular a good fit. In contrast, the chewing side of a dental restoration or a natural tooth is visible but aesthetics are primarily influenced by the general color than by color grading.

One or more aspects of visibility as described above may be implemented and used as placement information in the method according to the invention, in particular to reduce cost of producing a dental restoration.

Figure 5:
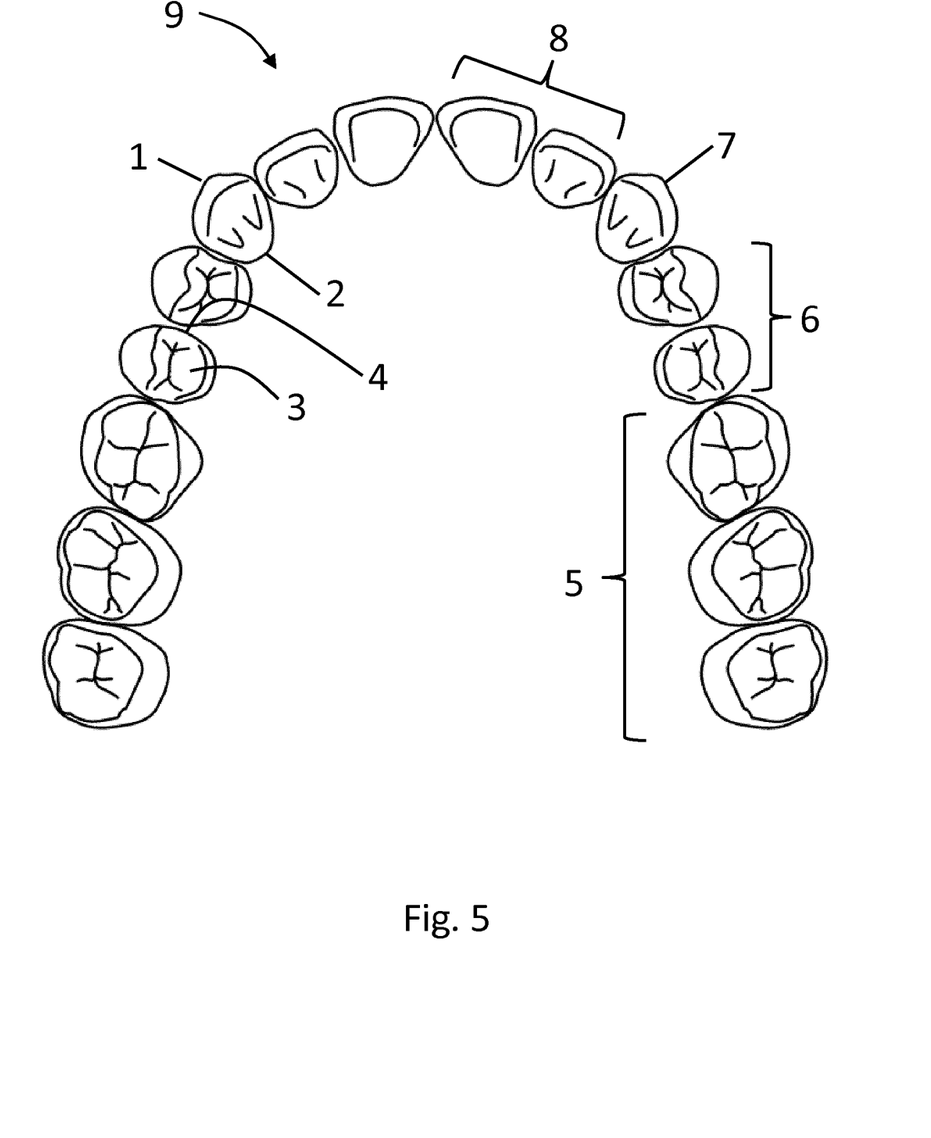
FIG. 5 illustrates a human dental arch.

FIG. 5 shows a human dental arch 9 comprising 16 teeth. Each tooth has a buccal side 1, a lingual side 2 and an occlusal surface 3. Interdental spaces 4 are present between adjacent teeth.

The dental arch 9 comprises molar teeth 5, pre-molar teeth 6, canine 7 and incisor teeth 8.

The invention claimed is:

1. A method for producing a dental restoration for at least a part of at least one tooth, the method comprising the steps of:
   including acquired data in design data, wherein the acquired data comprises placement information including a position and an orientation of the at least one tooth, the position and the orientation providing external visibility information of different sections of the dental restoration for an observer, wherein the acquired data is based on scan data of at least a portion of a patient's mouth;
   including preliminary design data in the design data, the preliminary design data comprising a design of the dental restoration that is not fixed;
   modifying the preliminary design data of the design data at least partly based on the acquired data comprising the placement information including the position and the orientation of the at least one tooth which includes the external visibility information of different sections of the dental restoration for an observer and before execution of at least one manufacturing step to obtain modified design data; and
   manufacturing the dental restoration based on the modified design data, wherein the placement information of the acquired data, including the position and the orientation of the at least one tooth of the modified design data and the external visibility information of different sections of the dental restoration for an observer, is used to determine a precision of manufacturing for one section relative to another section of the different sections of the dental restoration, wherein manufacturing comprises manufacturing portions of the at least one tooth that are more visible for an observer based on the external visibility information of different sections of the dental restoration with higher precision and level of detail than portions of the at least one tooth that are less visible for an observer,
   wherein the precision of manufacturing comprises a surface roughness of the at least one tooth.

2. The method according to claim 1, wherein a placement of support means for supporting the dental restoration during handling and/or production is automatically determined based on the placement information.

3. The method according to claim 1, wherein the placement information comprises information of at least one of buccal side; lingual side; visible portion; interdental space, or area of contact to other teeth.

4. The method according to claim 1, wherein the placement information and/or the preliminary design data comprise information about an occlusal surface.

5. The method according to claim 4, wherein the information about the occlusal surface comprises a level of precision and/or a level of detail dependent on the position of the at least one tooth.

6. The method according to claim 1, wherein manufacturing comprises manufacturing a visible buccal side of the at least one tooth with the higher precision and level of detail than a lingual side and an interdental side.

7. The method according to claim 1, further comprising a step of verifying the dental restoration, wherein the placement information is used to place the dental restoration in a measurement device in a required position to obtain measurement data by measuring the dental restoration.

8. The method according to claim 7, wherein the verifying step comprises comparing the measurement data and the design data and/or data derived from the design data to obtain at least one acceptability criterion.

9. The method according to claim 1, wherein the design data comprises shading data and/or color data of the at least one tooth.

10. The method according to claim 9, further comprising a step of providing data representing a blank comprising at least a portion made of a multilayered material and selecting a part of the blank based on the shading data and/or color data to produce the dental restoration from the blank.

11. The method according to claim 9, further comprising a step of providing data representing a blank comprising at least a portion made of a multilayered material and selecting a part of the blank based on a visible representation of the dental restoration comprised in the design data.

12. The method according to claim 1, further comprising a step of providing the design data.

13. The method according to claim 12, wherein the design data including the acquired data are generated with a computer program.

14. The method according to claim 1, wherein the acquired data of the design data are based on at least one of scan data, a photo and manually entered data of a dental situation of a patient.

15. The method according to claim 14, wherein the scan data comprise intra-oral scan data or extra-oral scan data.

16. The method according to claim 15, wherein the extra-oral scan data are generated with at least one of CT scanning and scanning of a model or impression of the dental situation of the patient.

17. The method according to claim 1, wherein the dental restoration is placed after production without veneering to obtain a desired shading and/or color of the at least one tooth.

18. The method according to claim 1, wherein modifying the preliminary design data is at least partly based on the acquired data.

19. The method according to claim 1, wherein the at least a part of at least one tooth comprises at least two teeth.

20. The method according to claim 1, wherein manufacturing comprises manufacturing an occlusal surface of a molar or pre-molar tooth with the higher precision and level of detail than an occlusal surface of a canine or an incisor tooth.

21. The method according to claim 6, wherein the visible buccal side of the at least one tooth comprises a buccal side of a frontal tooth.

* * * * *